United States Patent
Tanner, Jr. et al.

(10) Patent No.: US 10,366,204 B2
(45) Date of Patent: Jul. 30, 2019

(54) SYSTEM AND METHOD FOR DECENTRALIZED AUTONOMOUS HEALTHCARE ECONOMY PLATFORM

(71) Applicant: PokitDok, Inc., San Mateo, CA (US)

(72) Inventors: Theodore Tanner, Jr., San Mateo, CA (US); Timothy Scott Dunlevy, San Mateo, CA (US)

(73) Assignee: CHANGE HEALTHCARE HOLDINGS, LLC, Alpharetta, GA (US)

( * ) Notice: Subject to any disclaimer, the term of this patent is extended or adjusted under 35 U.S.C. 154(b) by 0 days.

(21) Appl. No.: 14/934,049

(22) Filed: Nov. 5, 2015

(65) Prior Publication Data

US 2017/0039330 A1    Feb. 9, 2017

Related U.S. Application Data (60) Provisional application No. 62/200,272, filed on Aug. 3, 2015.

(51) Int. Cl.
*G06F 19/00* (2018.01)
*G06F 21/64* (2013.01)

(52) U.S. Cl.
CPC .......... *G06F 19/328* (2013.01); *G06F 21/645* (2013.01)

(58) Field of Classification Search
CPC ........ G06Q 10/06; G06Q 10/10; G06Q 50/18; H04L 63/0227; H04L 67/1095
USPC ............................................................ 705/2
See application file for complete search history.

(56) References Cited

U.S. PATENT DOCUMENTS

| | | |
|---|---|---|
| 5,872,021 A | 2/1999 | Matsumoto et al. |
| 6,546,428 B2 | 4/2003 | Baber et al. |
| 7,386,565 B1 | 6/2008 | Singh et al. |
| 7,917,378 B2 | 3/2011 | Fitzgerald et al. |
| 7,917,515 B1 | 3/2011 | Lemoine |
| 7,970,802 B2 | 6/2011 | Ishizaki |
| 7,992,153 B2 | 8/2011 | Ban |
| 8,060,395 B1 | 11/2011 | Frasher et al. |
| 8,073,801 B1 | 12/2011 | Von Halle et al. |
| 8,095,975 B2 | 1/2012 | Boss et al. |
| 8,103,667 B2 | 1/2012 | Azar et al. |
| 8,103,952 B2 | 1/2012 | Hopp |
| 8,203,562 B1 | 6/2012 | Alben et al. |
| 8,229,808 B1 | 7/2012 | Heit |

(Continued)

FOREIGN PATENT DOCUMENTS

| | | |
|---|---|---|
| GB | 2478440 | 10/2013 |
| JP | 2002-189909 | 7/2002 |

(Continued)

OTHER PUBLICATIONS

Ahlswede et al., *Network Information Flow*, IEEE Transactions on Information Theory, vol. 46, No. 4; Jul. 2000 (13 pgs.).

(Continued)

*Primary Examiner* — Hiep V Nguyen
(74) *Attorney, Agent, or Firm* — DLA Piper LLP (US)

(57) ABSTRACT

A system and method for a decentralized autonomous healthcare economy platform are provided. The system and method aggregates all of the healthcare data into a global graph-theoretic topology and processes the data via a hybrid federated and peer to peer distributed processing architectures.

14 Claims, 8 Drawing Sheets

Abstracted High Level Process

(56) References Cited

U.S. PATENT DOCUMENTS

| | | |
|---|---|---|
| 8,286,191 B2 | 10/2012 | Amini et al. |
| 8,359,298 B2 | 1/2013 | Schacher et al. |
| 8,364,501 B2 | 1/2013 | Rana et al. |
| 8,417,755 B1 | 4/2013 | Zimmer |
| 8,495,108 B2 | 7/2013 | Nagpal et al. |
| 8,515,777 B1 | 8/2013 | Rajasenan |
| 8,527,522 B2 | 9/2013 | Baron |
| 8,817,665 B2 | 8/2014 | Thubert et al. |
| 8,984,464 B1 | 3/2015 | Mihal et al. |
| 9,165,045 B2 | 10/2015 | Mok et al. |
| 9,208,284 B1 | 12/2015 | Douglass |
| 2002/0022973 A1 | 2/2002 | Sun et al. |
| 2002/0038233 A1 | 3/2002 | Shubov et al. |
| 2002/0165738 A1 | 11/2002 | Dang |
| 2003/0055668 A1 | 3/2003 | Saran et al. |
| 2003/0097359 A1 | 5/2003 | Ruediger |
| 2003/0171953 A1* | 9/2003 | Narayanan ............ G06F 19/327 705/2 |
| 2003/0217159 A1 | 11/2003 | Schramm-Apple et al. |
| 2003/0233252 A1 | 12/2003 | Haskell et al. |
| 2004/0143446 A1 | 7/2004 | Lawrence |
| 2005/0010452 A1 | 1/2005 | Lusen |
| 2005/0071189 A1 | 3/2005 | Blake et al. |
| 2005/0102170 A1 | 5/2005 | Lefever et al. |
| 2005/0137912 A1 | 6/2005 | Rao et al. |
| 2005/0152520 A1 | 7/2005 | Logue |
| 2005/0182780 A1 | 8/2005 | Forman et al. |
| 2005/0222912 A1 | 10/2005 | Chambers |
| 2006/0036478 A1 | 2/2006 | Aleynikov et al. |
| 2006/0074290 A1 | 4/2006 | Chen et al. |
| 2006/0089862 A1 | 4/2006 | Anandarao et al. |
| 2006/0129428 A1 | 6/2006 | Wennberg |
| 2006/0136264 A1 | 6/2006 | Eaton et al. |
| 2006/0242140 A1 | 10/2006 | Wnek |
| 2007/0113172 A1 | 5/2007 | Behrens et al. |
| 2007/0118399 A1 | 5/2007 | Avinash et al. |
| 2007/0156455 A1 | 7/2007 | Tarino et al. |
| 2007/0174101 A1 | 7/2007 | Li et al. |
| 2007/0180451 A1 | 8/2007 | Ryan et al. |
| 2007/0214133 A1 | 9/2007 | Liberty et al. |
| 2007/0233603 A1 | 10/2007 | Schmidgall et al. |
| 2007/0260492 A1 | 11/2007 | Feied et al. |
| 2007/0276858 A1 | 11/2007 | Cushman et al. |
| 2007/0288262 A1 | 12/2007 | Sakaue et al. |
| 2008/0013808 A1 | 1/2008 | Russo et al. |
| 2008/0046292 A1 | 2/2008 | Myers |
| 2008/0082980 A1 | 4/2008 | Nessland et al. |
| 2008/0091592 A1 | 4/2008 | Blackburn et al. |
| 2008/0126264 A1* | 5/2008 | Tellefsen ............... G06Q 10/04 705/80 |
| 2008/0133436 A1 | 6/2008 | Di Profio |
| 2008/0215993 A1 | 9/2008 | Rossman |
| 2008/0288292 A1 | 11/2008 | Bi et al. |
| 2008/0295094 A1 | 11/2008 | Korupolu et al. |
| 2008/0319983 A1 | 12/2008 | Meadows |
| 2009/0083664 A1 | 3/2009 | Bay |
| 2009/0125796 A1 | 5/2009 | Day et al. |
| 2009/0164236 A1 | 6/2009 | Holcomb |
| 2009/0192864 A1 | 7/2009 | Song et al. |
| 2009/0198520 A1 | 8/2009 | Piovanetti-Perez |
| 2009/0300054 A1 | 12/2009 | Fisher et al. |
| 2009/0307104 A1 | 12/2009 | Weng |
| 2009/0313045 A1 | 12/2009 | Boyce |
| 2010/0017222 A1 | 1/2010 | Yeluri |
| 2010/0070303 A1 | 3/2010 | Massounuil |
| 2010/0076950 A1 | 3/2010 | Kenedy et al. |
| 2010/0082620 A1 | 4/2010 | Jennings, III et al. |
| 2010/0088108 A1 | 4/2010 | MacHado |
| 2010/0088119 A1 | 4/2010 | Tipirneni |
| 2010/0138243 A1 | 6/2010 | Carroll |
| 2010/0217973 A1 | 8/2010 | Kress et al. |
| 2010/0228564 A1 | 9/2010 | Kharraz |
| 2010/0228721 A1 | 9/2010 | Mok et al. |
| 2010/0295674 A1 | 11/2010 | Hsieh et al. |
| 2010/0332273 A1 | 12/2010 | Balasubramanian et al. |
| 2011/0009707 A1 | 1/2011 | Kaundinya |
| 2011/0015947 A1 | 1/2011 | Erry et al. |
| 2011/0047169 A1 | 2/2011 | Leighton |
| 2011/0055252 A1 | 3/2011 | Kapochunas et al. |
| 2011/0071857 A1 | 3/2011 | Malov et al. |
| 2011/0137672 A1 | 6/2011 | Adams et al. |
| 2011/0218827 A1 | 9/2011 | Kennefick et al. |
| 2011/0270625 A1 | 11/2011 | Pederson et al. |
| 2012/0004943 A1 | 1/2012 | Reichman |
| 2012/0011029 A1* | 1/2012 | Thomas ............ G06Q 30/0623 705/26.63 |
| 2012/0023107 A1 | 1/2012 | Nachnani |
| 2012/0035984 A1 | 2/2012 | Srinivasa et al. |
| 2012/0078940 A1 | 3/2012 | Kolluri et al. |
| 2012/0130736 A1 | 5/2012 | Dunston et al. |
| 2012/0158429 A1 | 6/2012 | Murawski et al. |
| 2012/0158750 A1 | 6/2012 | Faulkner et al. |
| 2012/0173279 A1 | 7/2012 | Nessa et al. |
| 2012/0245958 A1 | 9/2012 | Lawrence et al. |
| 2012/0246727 A1 | 9/2012 | Elovici et al. |
| 2012/0290320 A1 | 11/2012 | Kurgan et al. |
| 2012/0290564 A1 | 11/2012 | Mok et al. |
| 2013/0030827 A1 | 1/2013 | Snyder et al. |
| 2013/0044749 A1 | 2/2013 | Eisner et al. |
| 2013/0085769 A1 | 4/2013 | Jost et al. |
| 2013/0138554 A1 | 5/2013 | Nikankin et al. |
| 2013/0166552 A1 | 6/2013 | Rozenwald et al. |
| 2013/0204940 A1 | 8/2013 | Kinsel et al. |
| 2013/0290007 A1 | 10/2013 | Hag |
| 2013/0304903 A1 | 11/2013 | Mick et al. |
| 2013/0332194 A1 | 12/2013 | D'Auria |
| 2014/0046931 A1 | 2/2014 | Mok et al. |
| 2014/0056243 A1 | 2/2014 | Pelletier et al. |
| 2014/0059084 A1 | 2/2014 | Adams et al. |
| 2014/0088981 A1 | 3/2014 | Momita |
| 2014/0136233 A1 | 5/2014 | Atkinson et al. |
| 2014/0180727 A1 | 6/2014 | Freibreger |
| 2014/0207509 A1 | 7/2014 | Yu et al. |
| 2014/0222482 A1 | 8/2014 | Gautam et al. |
| 2014/0244300 A1 | 8/2014 | Bess et al. |
| 2014/0249878 A1 | 9/2014 | Kaufman et al. |
| 2014/0278491 A1 | 9/2014 | Weiss |
| 2014/0358578 A1 | 12/2014 | Ptachcinski |
| 2014/0358845 A1 | 12/2014 | Mundlapudi et al. |
| 2015/0006558 A1 | 1/2015 | Leighton |
| 2015/0095056 A1 | 4/2015 | Ryan et al. |
| 2015/0112696 A1 | 4/2015 | Kharraz Tavakol |
| 2015/0142464 A1 | 5/2015 | Rusin et al. |
| 2015/0142495 A1 | 5/2015 | Garakani |
| 2015/0154528 A1 | 6/2015 | Kharraz |
| 2015/0199482 A1 | 7/2015 | Corbin et al. |
| 2015/0332283 A1* | 11/2015 | Witchey ............ G06Q 30/018 705/3 |
| 2016/0028552 A1 | 1/2016 | Spanos et al. |
| 2016/0055205 A1 | 2/2016 | Jonathan et al. |
| 2016/0253679 A1 | 9/2016 | Venkatraman et al. |
| 2016/0261411 A1 | 9/2016 | Yau |
| 2016/0328641 A1 | 11/2016 | Alsaud et al. |
| 2016/0342750 A1 | 11/2016 | Alstad et al. |
| 2016/0342751 A1 | 11/2016 | Alstad et al. |
| 2017/0060856 A1 | 3/2017 | Turtle |
| 2017/0091397 A1* | 3/2017 | Shah ..................... G06F 19/322 |
| 2017/0103164 A1 | 4/2017 | Dunlevy et al. |
| 2017/0103165 A1 | 4/2017 | Dunlevy et al. |
| 2017/0132621 A1 | 5/2017 | Miller et al. |
| 2017/0351821 A1 | 12/2017 | Tanner et al. |
| 2017/0372300 A1 | 12/2017 | Dunlevy et al. |
| 2018/0082183 A1 | 3/2018 | Hertz |

FOREIGN PATENT DOCUMENTS

| | | |
|---|---|---|
| JP | 2003-303232 | 10/2003 |
| JP | 2008-234381 | 10/2008 |

(56) References Cited

FOREIGN PATENT DOCUMENTS

| JP | 2011-054045 | 3/2011 |
|----|-------------|--------|
| WO | WO 2012/122065 | 9/2012 |

OTHER PUBLICATIONS

Bhattacharya, Indrajit and Getoor, Lise, *Entity Resolution in Graphs*, Department of Computer Science, University of Maryland (2005) (21 pgs.).

Chen et al., *Adaptive Graphical Approach to Entity Resolution*, Jun. 18-23, 2007, Proceedings of the 7th ACM/IEEE-CS Joint Conference on Digital Libraries, pp. 204-213 (10 pgs.).

Christen, *Data Matching, Concepts and Techniques for Record Linkage, Entity Resolution, and Duplicate Detection*, © Springer-Verlag Berlin Heidelberg, 2012 (279 pgs.).

Cohen et al., *A Comparison of String Metrics for Matching Names and Records*, © 2003, American Association for Artificial Intelligence (www.aaai.org) (6 pgs.).

Coleman et al., *Medical Innovation—a diffusion study*; The Bobbs-Merrill Company, Inc., 1966 (248 pgs.).

Domingos et al., *Mining High-Speed Data Streams*, (2000) (10 pgs.).

Greenhalgh et al., *Diffusion of Innovations in Health Service Organisations—a systematic literature review*, Blackwell Publishing, 2005 (325 pgs.).

Jackson et al., *The Evolution of Social and Economic Networks*, Journal of Economic Theory 106, pp. 265-295, 2002 (31 pgs.).

Jackson, Matthew O., *Social and Economic Networks*, Princeton University Press, 2008 (509 pgs.).

Krempl et al., *Open Challenges for Data Stream Mining Research*, SIGKDD Explorations, vol. 16, Issue 1, Jun. 2014 (64 pgs.).

Lin et al., *A simplicial complex, a hypergraph, structure in the latent semantic space of document clustering*, © Elsevier, 2005 (26 pgs.).

Rebuge, *Business Process Analysis in Healthcare Environments*, 2011, Ellsevier Ltd., pp. 99-116 (18 pgs.).

Wasserman et al., *Social Network Analysis: Methods and Applications*, Cambridge University Press; 1994 (434 pgs.).

White et al., *Algorithms for Estimating Relative Importance in Networks*, Proceedings of the Ninth ACM SIGKDD International Conference on Knowledge Discovery and Data Mining, 2003 (10 pgs.).

(MATHJAX), *Naive Bayes Categorisation (with some help from Elasticsearch)*, blog post dated Dec. 29, 2013 (https://blog.wtf.sg/2013/12/29/naive-bayes-categorisation-with-some-help-from-elasticsearch/). (8 pgs.).

Webpage: New Health Care Electronic Transactions Standards Versions 5010, D.0, and 3.0, Jan. 2010 ICN 903192; http://www.cms.gov/Regulations-and-Guidance/HIPAA-Adminstrative-Simplification/Versions5010andD0/downloads/w5010BasicsFctCht.pdf (4 pgs.).

Webpage: U.S. Dept. Of Health and Human Services, Guidance Regarding Methods for De-identification of Protected Health Information in Accordance with the Health Insurance Portability and Accountability Act (HIPAA) Privacy Rule, http://www.hhs.gov/ocr/privacy/hipaa/understanding/coveredentities/De-identification/guidance.html printed Oct. 15, 2015 (14 pgs.).

Anonymous: "Oauth—Wikipedia", Sep. 23, 2013. Retrieved from the Internet URL:https://en.wikipedia.org/w/index.php?title+oAuth&oldid+574187532 (3 pages).

Version 5010 and D.O, Center for Medicare & Medicaid Services (2 pgs.).

Anonymous: "Oauth" Wikipedia—Retrieved from the Internet URL:https://en.wikipedia.org/wiki/Oauth (8 pgs.).

\* cited by examiner

Figure 1.0 Abstracted High Level Process

FIGURE 1B

Fig 2.0. Health BlockChain Application

Figure 3.0 Blockchain

Figure 4.0 Referral Workflow

Figure 5.0 Patient Behavior Health Plans

Figure 6.0 Patient and Provider Data Sharing

Figure 7.0 Patient Data Sharing

10,366,204 B2

SYSTEM AND METHOD FOR DECENTRALIZED AUTONOMOUS HEALTHCARE ECONOMY PLATFORM

PRIORITY APPLICATIONS/RELATED APPLICATIONS

This application claims the benefit under 35 USC 119(e) and priority under 35 USC 120 to U.S. Provisional Patent Application No. 62/200,272, file Aug. 3, 2015 and titled "System and Method for Decentralized Autonomous Healthcare Economy Platform", the entirety of which is incorporated herein by reference.

FIELD

The disclosure relates generally to a healthcare system.

BACKGROUND

The healthcare industry currently has a number of issues that need to be resolved including
   The speed at which basic transactions occur in health information networks.
   The siloed nature of information contained within these health information networks.
   The ability for the consumer to gain access to the flow of health information contained in these networks.
   The reliability and traceability of transactions in health information networks.
   The need for seamless interoperability within the Health industry is of utmost concern. This includes all aspects of the consumer, payer and provider landscape. Healthcare enterprise applications (e.g. Electronic Medical Record systems (EMRs), Electronic HealthCare Records (EHRs), Practice Management systems (PMs) and payor solutions) have been created within many areas of healthcare information technology to supposedly address specific end user (consumer) requirements. However these applications do not allow for interoperability and transparency of data operations.

For example, the EMR(s) exist as islands of information with little or no connectivity between the plethora of product offerings. This has been further exacerbated with the usage of Electronic Data Interchange "standards" such as ASC 4010/5010 X12 (further details of which are found at http://www.x12.org/which is incorporated herein by reference.) Further, the process deepens within the same hospital system and what connectivity has been implemented has been a largely manual effort with significant costs in implementation and maintenance, further exacerbating the situation. This scenario gives way to an Application Programming Interface (API) system that is REST based and that is multi-tenancy. Multi-tenancy is an architecture in which a single instance of a software application serves multiple customers. Each customer is called a tenant. With multi-tenancy, scaling has far fewer infrastructure implications for vendors (depending on the size of the application and the amount of infrastructure required). Further, a multitenant software system is a system that supports any number of customers within a single application instance. Typically, that single instance makes use of a shared data set(s), where a customer's data is properly separated from another's. While data separation is a crucial aspect of a multitenant application, there may be system-wide (e.g. global) computations that require the consumption of all customer data (or some subset thereof). If no such global operations are required, then a multitenant application would instead be a multi-instance application, where each customer's data is contained in its own isolated silo.

According to the Healthcare Information and Management Systems Society (HIMSS-details of which are at http://www.himss.org/which is incorporated herein by reference), analytics organization, larger countries (such as the United States, Canada, Germany, France, Italy and Spain) are behind several smaller European countries (such as Denmark, Holland and Sweden) in reaching the highest level of paperless data sharing, storage and decision support according to Uwe Buddrus, HIMSS Analytics Europe, personal communication. The number of faxes per year in healthcare in the United States alone approach 15(million) annually. There is a hard line requirement to reduce the paper interactions and move to more fluid electronic formats.

BRIEF DESCRIPTION OF THE DRAWINGS

FIG. 1.0 is a system 100 for decentralized healthcare that has a peer to peer architecture;
FIG. 2.0 illustrates an examples of a healthcare blockchain application that is part of the decentralized system;
FIG. 3.0 illustrates an example of a healthcare blockchain;
FIG. 4.0 illustrates an example of a referral workflow of the decentralized healthcare block chain system;
FIG. 5.0 illustrates an example of a process for patient behavior health plan;
FIG. 6.0 illustrates a patient and provider data sharing process of the of the decentralized healthcare block chain system;
and
FIG. 7.0 illustrates patient data sharing data flow using the decentralized system.

DETAILED DESCRIPTION OF ONE OR MORE EMBODIMENTS

The system and method described below aggregates all of the healthcare data into a global graph-theoretic topology and processes the data via a hybrid federated and peer to peer distributed processing architecture (which are further details of which are described at https://en.wikipedia.org/wiki/Peer-to-peer and https://en.wikipedia.org/wiki/Peer-to-peer which are incorporated herein by reference.) Some of the data contained in these processes may include but are not limited to:
   Patient records in a multitenant electronic health record system can be separated to ensure patient confidentiality. However, collective de-identified statistics can be gleaned from the global data set in order to allow data analysts/scientists to study population-wide health concerns.
   Claims, benefits and referral information
   Wearable data such as BMI and heart rate
   Amount billable or bill to information concerning transactions for the respective corporation
   Gives the consumer the ability to truly control their medical and health information via a single permanent ledgered identity managed system.
The system and method may implement the models of Electronic Data Interchange (EDI) under ASC X12 in several differing manners and programmatic methodologies. The following are some of the hurdles:
   Most hospitals still have obsolete or proprietary standards or protocols running as their critical applications.

Healthcare standards are under constant development and improvements.

Divergent not convergent HealthCare standards are such as:

- HL7 v2.x, v3 (further details of which are described at http://www.hl7.org/which is incorporated herein by reference)
- CEN TC/251 (further details of which are described at https://en.wikipedia.org/wiki/CEN/TC_251 which is incorporated herein by reference)
- openEHR (further details of which are described at http://www.openehr.org/which is incorporated herein by reference)
- ASC X12 4010/5010 (further details of which are described at http://www.x12.org/x12org/docs/EDI-Transactions.pdf which is incorporated herein by reference)
- SNOW-MED (further details of which are described at (http://www.nlm.nih.gov/research/umls/Snomed/snomed_main.html which is incorporated herein by reference)
- FHIR (further details of which are described at http://wiki.hl7.org/index.php?title=FHIR which is incorporated herein by reference)

All of these standards have intended semantics, however they do not follow the standard(s) with respect to the meanings of the data structure(s), thus defeating the purpose of said standards and therefore interoperability. For example, data is embedded in comment fields in an unstructured manner rather than using the prescribed data elements and structure.

Healthcare standards formatted in Extensible Markup Language (XML) and XSDs solve the integration or interoperability problem at a syntactic level, but domain specific solutions are required to achieve meaningful integration however the actual interchange, maintainability and scale are sub-optimal. They are also not scalable.

JavaScript Object Notation (JSON) has resulted in a better readable standard however the data model and schemas from the standards above are constantly shifting.

Thus, current healthcare enterprise applications need greater flexibility and scalability to meet the challenges of heterogeneity of healthcare systems at all levels—data, process, services, and payments. The architecture of any integration system holds the key to offer a dynamic, flexible and scalable solution.

The system and method uses an Agent/Actor model for data processing and observations (further details of which are described at http://c2.com/cgi/wiki?ActorVsAgent which is incorporated herein by reference.) The agent/actor model includes vendors, standards, legacy systems, and information systems all of which must interoperate to provide healthcare services. The system and method provide an interoperability solution without imposing any constraint on existing or proposed health systems. The major advantage of our approach is that it is a hybrid federated and decentralized system that is resilient and autonomous and requires no pre-approved or administrative overhead for participating in the HealthCare network. Further it affords payors, providers and consumers the ability to have access to the consumers data, given the consumer's granted consent, as well as provide the consumer the ability to maintain real time access and control of their personal health record (PHR).

Ideally, EHR/EMRs capture and integrate data on all aspects of care over time, with the data being represented according to relevant data structures and provide in real time the consumer access to the PHR. Currently this is not the case. The system and method and its processing architecture and model of data access will allow accurate data to flow within the system and provide transparent behaviors and access across the system.

Much of the data that is captured in EHR/EMR systems serve administrative purposes, such as monitoring hospital activity and performance, and government or insurance reimbursement. Even simple EHR/EMR systems will typically capture demographic patient information such as age, gender, ethnicity and address, as well as structured information about a given encounter in the form of dates and CPT (Current Procedural Terminology) and ICD (International Classification of Diseases) encoded services and diagnoses (often referred to as billing codes for both inpatient and outpatient). Most often these coding schemas are not automated and are prone to user error as well as double charge processes. This double charge process is often the culprit when processing claims information. Further the double charge in a ledger is also an artifact and error of processes within historical electronic banking systems whereas the ledger does not de-duplicate the ledger of record.

The system and method provide and use identity management that allows immediate access to the consumers PHR that could integrated with various different health applications, such as for example, Fit-Bit, Jawbone, Apple Apple Health Kit or PayPal. The system and method also provide peer to peer autonomous accurate health information exchange and transactional processing that will allow real time processing as well as immediate access and interoperability.

Exemplary Implementation Overview

Figure 10:
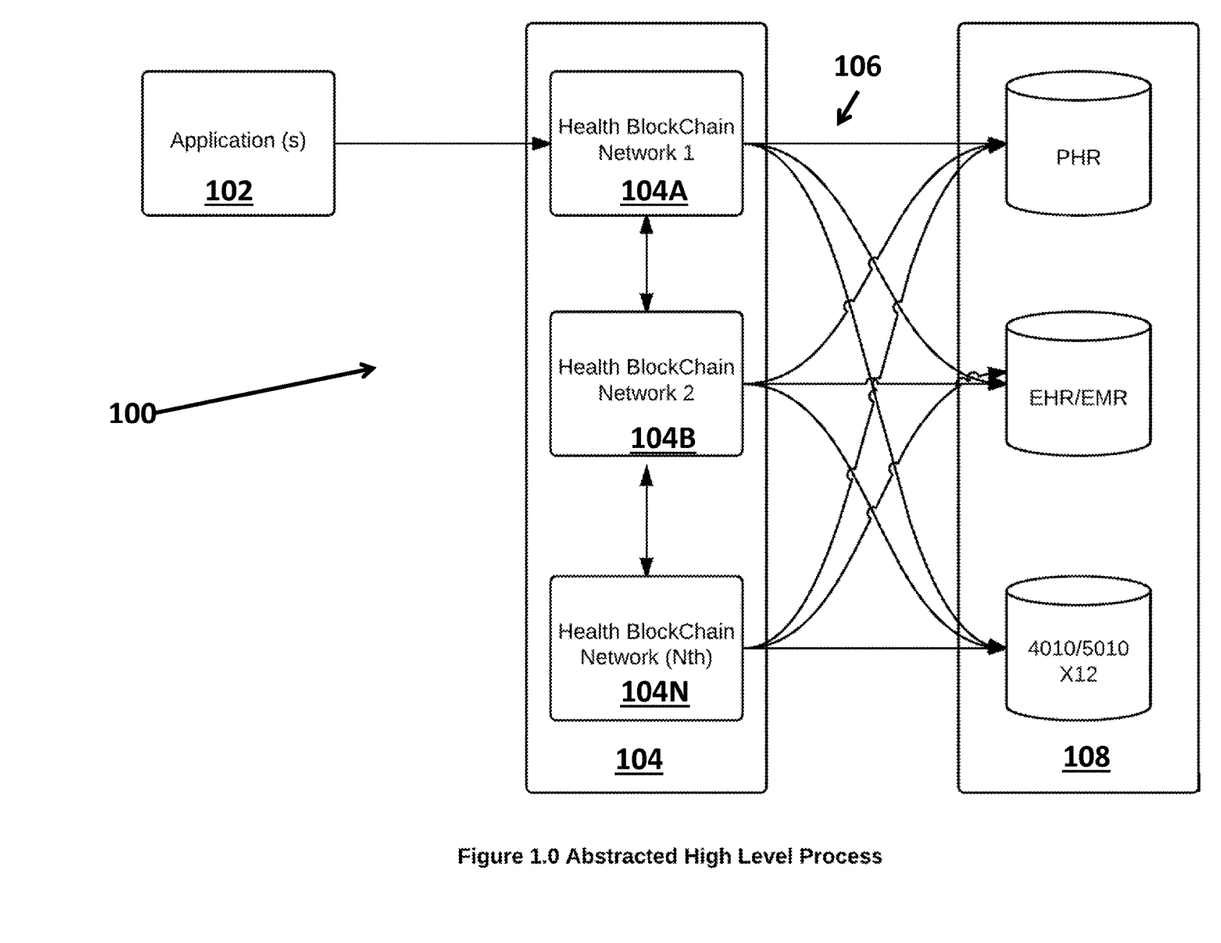

FIG. 1.0 illustrates a system 100 for decentralized healthcare that has a peer to peer architecture. A functional graph topology describes the semantics required for interaction between respective systems, based on the interaction events within healthcare standards which in our case is various standard data structures such as HL7, SNOW-MED, openEHR, FHIR and ASC X12 4010/5010 to provide domain based workflows between systems. The peer to peer taxonomy defines the transactional semantics associated with healthcare messages and interactions required to be exchanged for data interoperability between various systems. Differences in these specifications are resolved by peer to peer data mapping techniques as described below. The adapter framework receives the provenance rules developed at design-time and executed at run-time in an arbitrage fashion. An architecture that defines this model is termed blockchain. Blockchain was first discussed in the paper Bitcoin: A Peer-to-Peer Electronic Cash System by Satoshi Nakamoto (that is described in more detail at https://en.bitcoin.it/wiki/Wallet which is incorporated herein by reference. The system has a model of electronic payment system based on cryptographic proof instead of trust, allowing any two willing parties to transact directly with each other without the need for a trusted third party. The system leverages upon the basic concepts which allow a system to utilize the block chain topology in four basic fashions:

- All Business Associate Agreement HIPAA compliant information data is updated via the blockchain ledger process
- Data structures referenced within the block chain are written and updated via a distributed file process
- Personal Health Record information is stored in the person's 'bitcoin based' wallet architecture Arbitrage or bid/ask mechanics for connections to services that the respective data modules need from an agent based solution.

As shown in FIG. 1.0, the system 100 may have one or more applications 102 that need to access a backend system 104 over a communications path 106 wherein the backend system 104 may have one or more health block chain network components 104A, 104B, ..., 104N for example and the one or more applications access the one or more health block chain network components. Each application 102 may be executed by a computing device. Each computing device may be a processor based device that is able to connect to and interact with the backend 104 over the communications path 106 using known communications and data protocols and APIs. For example, each computing device may be a smartphone device such as an Apple iPhone or Android operating system based device, a personal computer, a laptop computer, a server computer, a terminal and the like that is able to execute the application 102 and perform the interactions with the health block chain network components.

The backend 104 and the health block chain network components may be implemented using one or more computing resources such as server computers, blade servers, mainframe computers, processors, memory, storage devices and the like. The backend 104 and the health block chain network components may be coupled to one or more health data sources 108 over the communications path 106. The backend 104 and the health block chain network components may communicate with the health data sources using the standards, protocols and/or APIs for each data source. In the example in FIG. 1.0, the health data sources may be a PHR system, an HER/EMR system and X12 based system.

As described above, one or more applications 102, such as host applications, that can access the Health BlockChain Network components 104A-104N. The Networks can be manifold in nature from a processing standpoint however focus on three main areas of processing for the (1) for the payer where there is a need to processing pricing data, eligibility, claims and benefits processing data (2) for the provider where there is a need for electronic medical/health records, scheduling and clinical, diagnosis and payment data (3) for the consumer where there is a need for the personal health record, scheduling information and payment data. This is illustrated via the host applications 102 that could cover the above scenarios and the blockchain processing which is a hybrid federated and decentralized and a file system which is distributed in nature.

Figure 1B:
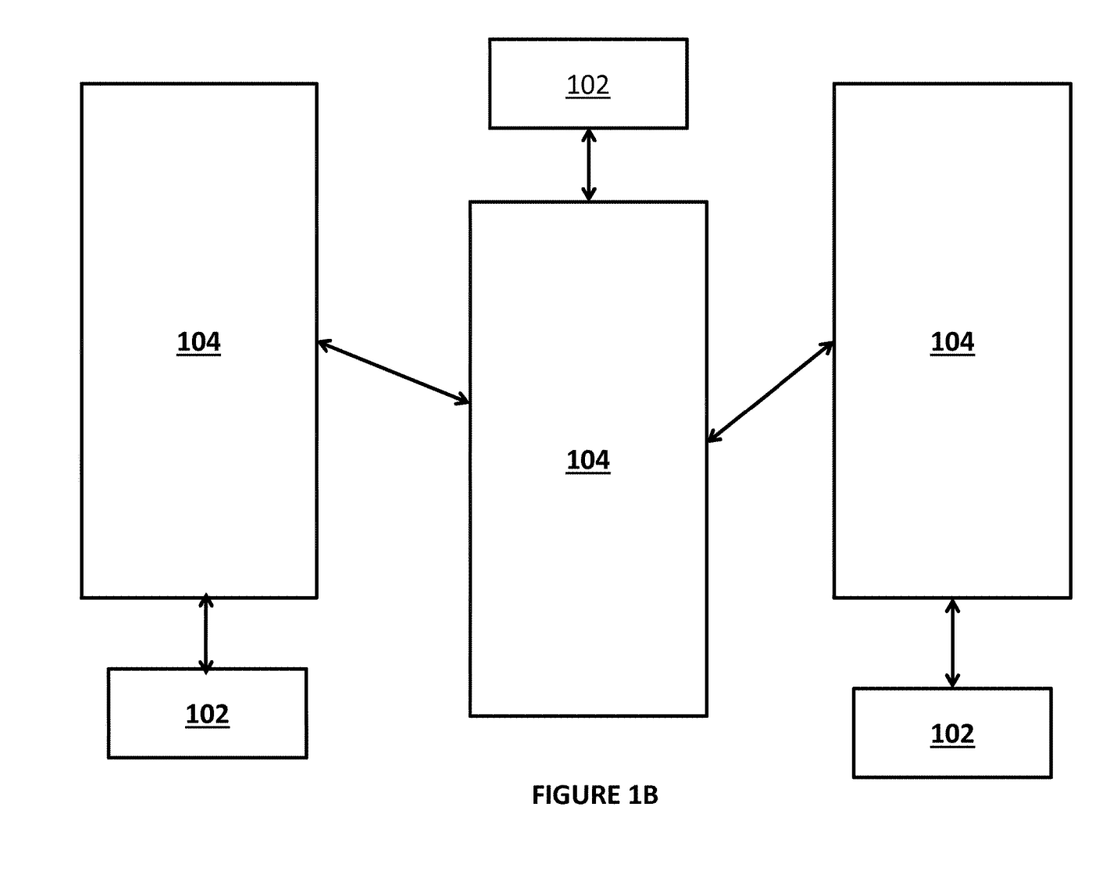
FIG. 1B illustrates an example of a computer system implementation of the decentralized system.

FIG. 1B illustrates an example of a computer system 100 implementation of the decentralized system. The decentralized peer to peer heathcare system and method may be implemented using various different types of computing resources including server computers, blade resources, database servers, application services, blade servers and any other computing resources including processor(s), memory, storage capabilities, communication capabilities and the like.

As shown in FIG. 1B, each computer system 104 may be interconnected and each application 102 may couple to and communicate with any computer system 104 various various secure and unsecure connection and data protocols. As described, each computer system 104 may have one or more Health BlockChain Network components 104A-104N that operate as described below.

Figure 20:
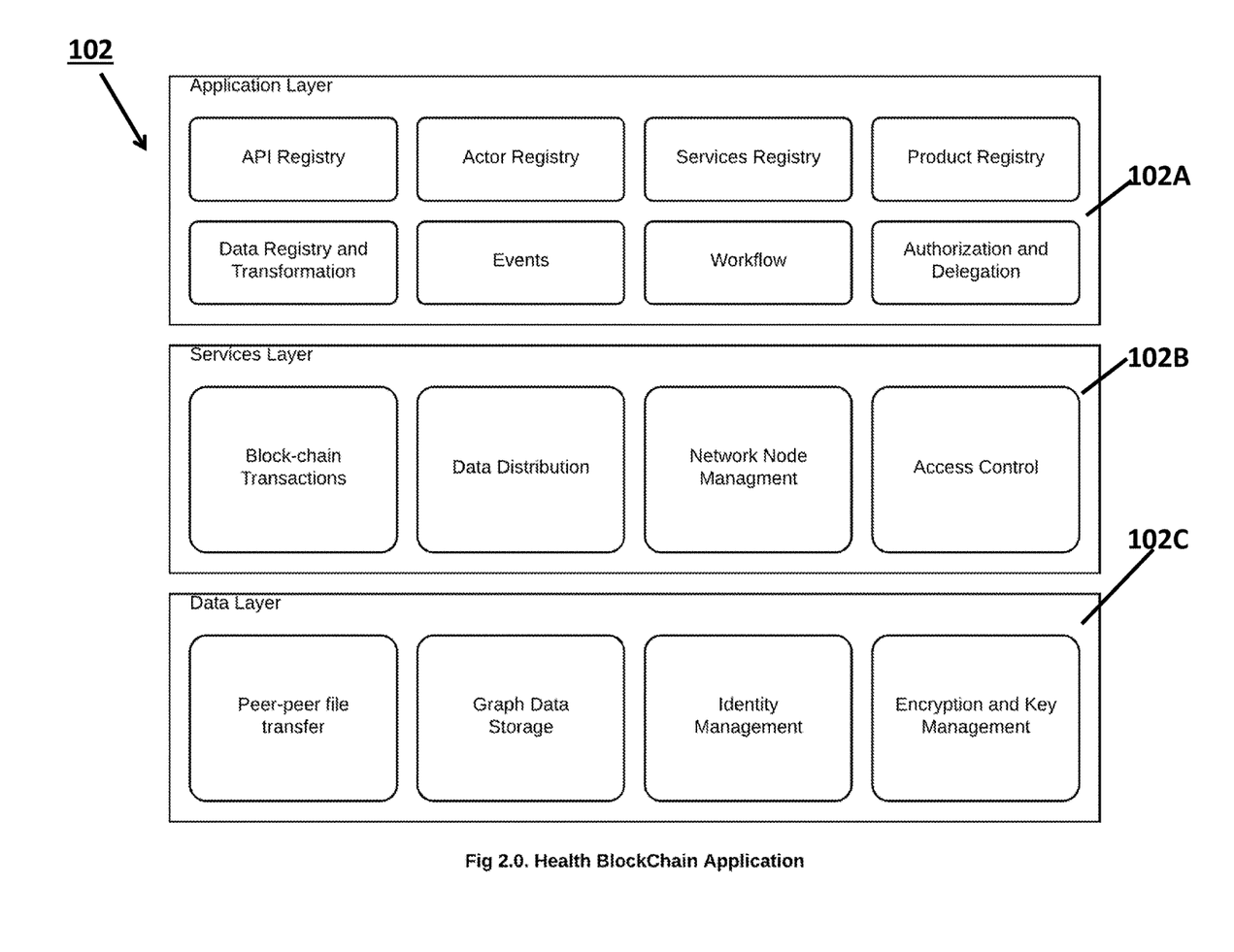

The application(s) 102 which utilize the Health BlockChain network(s) will facilitate the access, storage and distribution of health data, PHR/EHR/EMR, as well as health transactions, X12/Clinical and may be known as a health block chain application. An example of an application stack for each application 102 is shown in FIG. 2.0. Each application stack includes an application layer 102A, a services layer 102B and a data layer 102C. Since only resource identifiers (described in more detail at haps://tools org/html/rfc3986 that is incorporated herein by reference), asset signatures (described in more detail at https://github-.com/OpenAssets/open-assets-protocol/blob/master/specification.mediawiki#protocol-overview that is incorporated herein by reference) and authorization grants (described in more detail at https://tools.ietf.org/html/rfc6749#section-1.3 that is incorporated herein by reference) are stored in the Health Blockchain, the resources themselves and access to them is handled by participating applications. Depending upon the scope of the application a smaller subset of the identified components may be implemented for a specific implementation scenario. In the example shown in FIG. 2.0, the application layer 102A may include an API registry, an actor registry, a services registry, a product registry, a data registry and transformation, events, workflow and authorization and delegation. The services layer 102B may include block-chain transactions, data distribution elements, network node management and access control. The data layer 102C may include peer to peer file transfer, graph data storage, identity management and encryption and key management elements.

Figure 30:
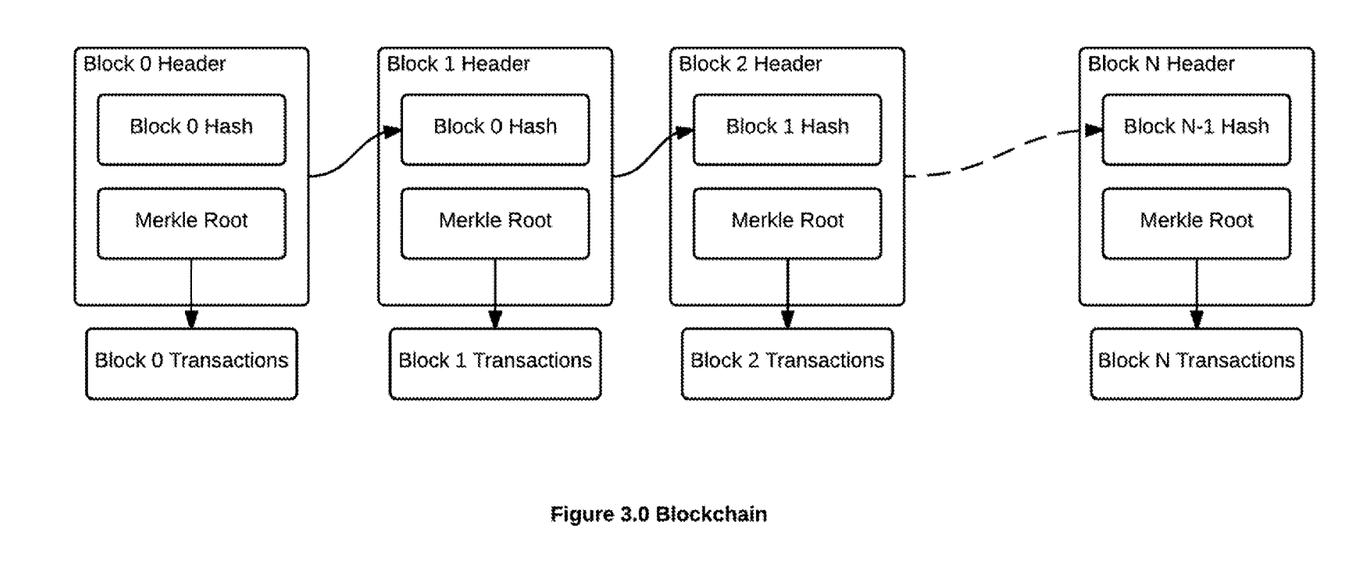

The Health Blockchain itself is organized as a distributed database of data blocks, or replicated shared ledger, in a constantly growing linked list, where each block is cryptographically verified by multiple nodes on the network. The structure and relationships of the block database is shown in FIG. 3.0. As shown, each block header 300 holds some of the data of the distributed database and block hash and a Merkle root. Each block header is connected to a block transaction and its data.

The data structure for the block structure is depicted in Table 1.0 and Table 1.1 below:

TABLE 1.0

| block structure of top level data - The Block: | | |
| --- | --- | --- |
| Field | Description | Size (B) |
| block_id | block identifier | 4 |
| block_size | number of bytes following | 4 |
| block_version | block version | 4 |
| hash_prev_block | 256 bit hash of previous block | 32 |
| hash_merkle_root | 256 bit hash of this block | 32 |
| Timestamp | seconds since 1970-01-01T00:00 UTC | 4 |
| Target | 256 bit number that hash must be less than | 32 |
| Nonce | 32 bit | 4 |
| transaction_counter | # of transactions | 1-9 (B) |
| transaction_data | transaction record data | variable |

To verify that inputs are authorized to collect the values of referenced outputs, a built-in scripting language is used. This scripting language is Turing-complete, stack-based and processed from left to right. The script language is typically written in a high level language (for example, solidity https://ethereum.github.io/solidity/docs/home/) and then compiled into the raw opcodes included in the blockchain transaction (pseudo-code representing this high-level language is used throughout this document in example transactions). The transaction inputs are authorized if the executed script returns true. Through the scripting system, the sender can create very complex conditions that actors in the system must meet in order to claim the output. In this way any automated system of checks, authorizations, actions or even external events can be involved and validated as part of the transaction.

The transaction data may consist of a Colored Coin implementation (described in more detail at https://en.bitcoin.it/wiki/Colored_Coins which is incorporated herein by reference), based on Open Assets (described in more detail at https://github.com/OpenAssets/open-assets-protocol/blob/master/specification.mediawiki which is incorporated herein by reference), using on the OP_RETURN operator. Metadata is linked from the Blockchain and stored on the web, dereferenced by resource identifiers and distributed on public torrent files. The colored coin specification provides a method for decentralized management of digital assets and smart contracts (described in more detail at https://github.com/ethereum/wiki/wiki/White-Paper which is incorporated herein by reference.) For our purposes the smart contract is defined as an event-driven computer program, with state, that runs on a blockchain and can manipulate assets on the blockchain. So a smart contract is implemented in the blockchain scripting language in order to enforce (validate inputs) the terms (script code) of the contract.

The digital assets are managed, transferred or involved in a smart contract. Payers issue assets such as a benefits data, or eligibility information. Providers issue assets for clinical documents, health records which the consumer may receive and grant access to through the use of smart contracts.

TABLE 1.1 block structure of the transaction

| Field | Description | Size |
| --- | --- | --- |
| OP_RETURN opcode | The OP_RETURN opcode (0x6a). | 1 byte |
| PUSHDATA opcode | The PUSHDATA opcode required to push the full payload onto the stack (0x01 to 0x4e, depending on the size of the payload). | 1-5 bytes |
| Open Assets Payload | See below. | Variable |
| The transaction payload may contain the following data types and fields: | | |
| OAP Marker | A tag indicating that this transaction is an Open Assets transaction. It is always 0x4f41. | 2 bytes |
| Version number | The major revision number of the Open Assets Protocol. For this version, it is 1 (0x0100). | 2 bytes |
| Asset quantity count | A var-integer representing the number of items in the asset quantity list field. | 1-9 bytes |
| Asset quantity list | A list of zero or more LEB128-encoded unsigned integers representing the asset quantity of every output in order (excluding the marker output). | Variable |
| Metadata length | The var-integer encoded length of the metadata field. | 1-9 bytes |
| Metadata | Arbitrary metadata to be associated with this transaction. This can be empty. | Variable |

Usage Scenarios

The above block chain processing and system shown in FIGS. 1.0, 2.0 and 3.0 may be used to process various health data and health transactions.

The system specifically deals with utilizing "side chaining" to process the private or semi-private smart contracts between the seller and buyers. A sidechain is a blockchain that validates data from other blockchains. These are implemented via "pegging." A pegged sidechain is a sidechain whose assets can be imported from and returned to other chains; that is, a sidechain that supports two-way pegged assets. Two-way peg refers to the mechanism by which (in our case) assets are transferred between sidechains and back at a fixed or otherwise deterministic exchange rate which is based on contextual rate of transfer or value in the case of our trade or arbitrage asset environment.

The specific nature of implementation of the system and method are based upon a networked graph based structure that is input into the "Health BlockChain" distributed process. This networked environment also allows for the basis of exchange models based on exchange theory. The algorithms sub-divides our graph of the distributed network into sub-graphs: those in which a set of sellers are collectively linked to a larger set of buyers (sellers obtain payoffs in a game-theoretic sense close to 1) and buyers receive payoffs near 0; those in which the collective set of sellers is linked to a same size collective set of buyers (each receive a payoff of about ½); and those in which sellers outnumber buyers (sellers receive payoffs near 0 and buyers obtain payoffs close to 1).

With respect to the architecture and data processes, the system updates using an exchange process based on former work by Corominas-Bosch and which processes exchange mechanics link patterns represent the potential transactions, however, the transactions and prices are determined by an auction rather than bargaining. In the case of the general model there are n sellers and m buyers of a homogenous good for which all sellers have reservation value 0 and all buyers have reservation value 1. Each buyer desires only one unit of the good, and each seller can supply only one unit. Is the price dependent only on the relative sizes of n and m, and will all trades take place at the same price? Here buyers (sellers) bargain with a pre-assigned subset of all sellers (buyers); links are non-directed, which means that A is linked to B if and only if B is linked to A. Any buyer may be connected to multiple sellers and vice versa. The network structure is common information, as are all proposals and acceptances. In our case of the reduction to practice our homogenous good is the respective connections, business agreements or service level agreements with respect to accessing said data within the blockchain.

In particular, prices rise simultaneously across all sellers. Buyers drop out when the price exceeds their valuation (as they would in an English or ascending oral auction). As buyers drop out, there emerge sets of sellers for whom the remaining buyers still linked to those sellers is no larger than the set of sellers. Those sellers transact with the buyers still linked to them. The exact matching of whom trades with whom given the link pattern is done carefully to maximize the number of transactions. Those sellers and buyers are cleared from the market, and the prices continue to rise among remaining sellers, and the process repeats itself. When the market price is cleared the agent updates the graph or subgraph and the ledger or ledgers in the blockchain are updated. The main agent based graph process splits the links into sub-graphs allowing faster processing and the payoffs in the network are based on game-theoretic probabilities as follows:

Step 1a: Identification of two or more sellers who are all linked to the same prospective buyer. Regardless of the buyers other links within the graph the method eliminates that set of sellers and buyer; the buyer then obtains a payoff or 1 and the sellers receive payoff of 0

Step 1b: Of the remaining network repeat step 1a with buyers and sellers reversed to balance the network     Step k: Proceed inductively in k, each time making identifications within the sub graphs of the subsets of at least k sellers are you collectively linked to some set of fewer-than-k buyers or some collection of at least k buyers who linked within the graph to some set of fewer-than-k sellers. k is the max of the network node processes in our case.

End: When the method iterates through and identify all of the subgraphs and remove them the buyers and sellers in the remaining network are such that every subset of sellers and buyers is linked to as many buyers and vice versa where the buyers and sellers in that subnetwork reach agreement and achieve a Nash Equilibrium of ½ payoff each within the subnetwork. This we believe also results Pareto Optimality With respect to our network, it has a very simple process for finding the equilibrium in the market such that the ledger clears and makes the market price in our case:

A buyer purchasing from multiple sellers sees the same price from each of the respective sellers.

The price of given seller is found by computing for each buyer the faction of the buyers total purchases that come from that seller and then summing across buyers.

The price of a given seller is no higher than the seller's degree centrality within the network and no lower than 1/min degree(num_buyers) connected to the seller.

Health Care EDI Transactions (ASC X12 4010/5010)

Processing health care transactions currently consists of manual agreements covering point-point solutions. These connections take significant effort from technical and administrative personnel to setup and maintain. In this scenario the proposed public blockchain solution can facilitate an automatic smart contract to cover a transaction as well as automatic service-level-agreement based selection of a trading partner to fulfill a request.

Figure 40:
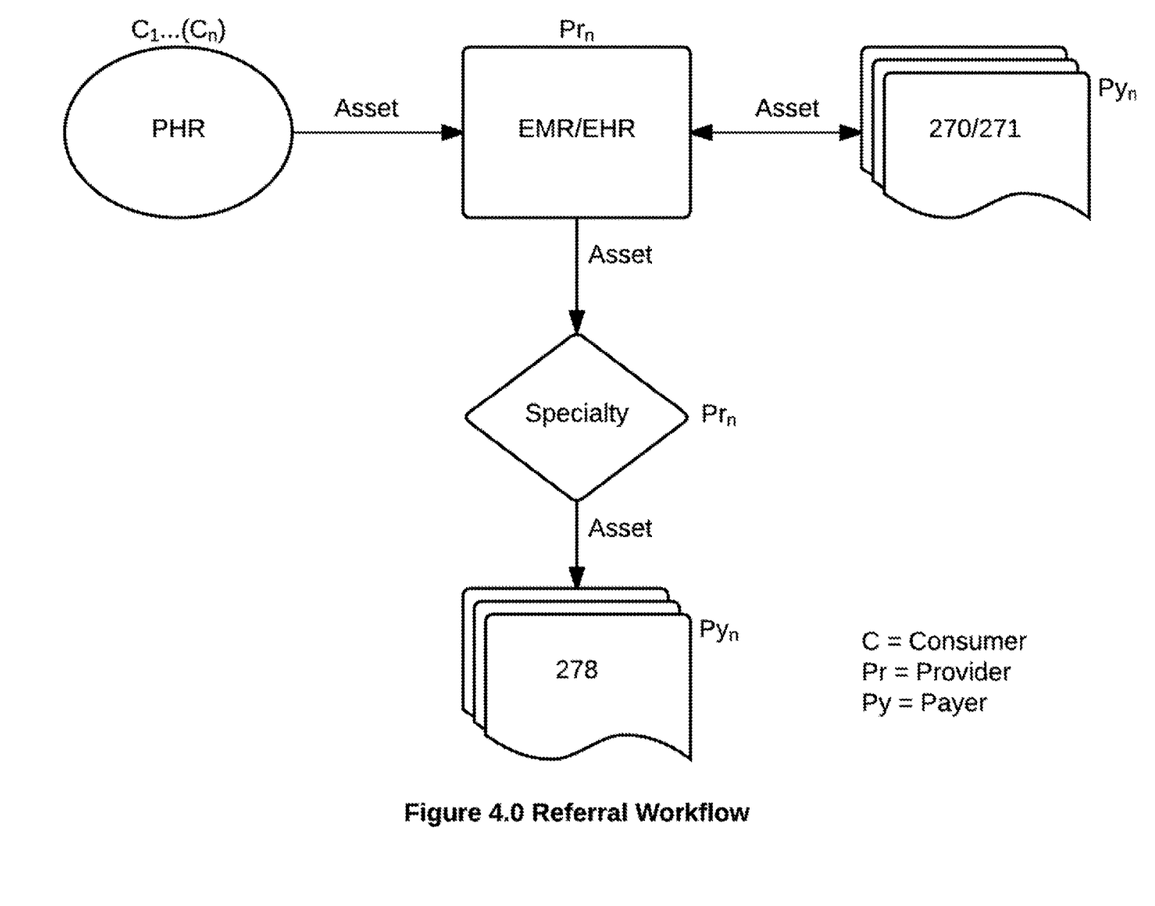

An example of a typical workflow for a referral is shown in FIG. 4.0. This scenario is fulfilled by several blockchain transactions where the assets of an individual's personal health record (PHR) and an eligibility check and response (X12 270/271) are combined with a provider's specialty as input to the referral (X12 278). Using the Health BlockChain network these transactions can be advertised as transactions with pending inputs. Providers participating in the network can satisfy the pending inputs with appropriate providers (assets) having necessary specialties. Payers, or clearinghouses acting on behalf of a payer under a smart contract, can satisfy pending inputs of necessary eligibility inputs (assets). Once the pending inputs are all satisfied the transactions will be validated and committed to the next block in the permanent blockchain ledger.

The pseudo code for the smart contract to implement the typical ASC X12 referral transaction is as follows.

Eligibility Transaction

```
user_info = transaction.data.user_input
payer = transaction.data.payer_input
if payer.fee <= 0 then
    eligibility_output =
    payer.eligibility.invoke(user_info)
    return eligibility_ output
```

PHR Transaction

```
user_info = transaction.data.user_input
provider = transaction.data.provider_input
if provider.is_authorized(user_info) then
    phr_output = provider.get_user_phr(user_info)
    return phr_output
```

Referral transaction, receives inputs of outputs from Eligibility and PHR transactions

```
eligibility_data = transaction.data.eligibility_input
phr_data = transaction.data.phr_input
specialty = transaction.data.provider.specialty_input
if eligibility_data.is_valid( ) and phr_data.is_valid( ) and
specialty = "ENT" then
    transaction.data.provider.referral.invoke(eligibility_
    data, phr_data)
```

Patient Behavior and Risk Pool Rated Health Plans

Figure 50:
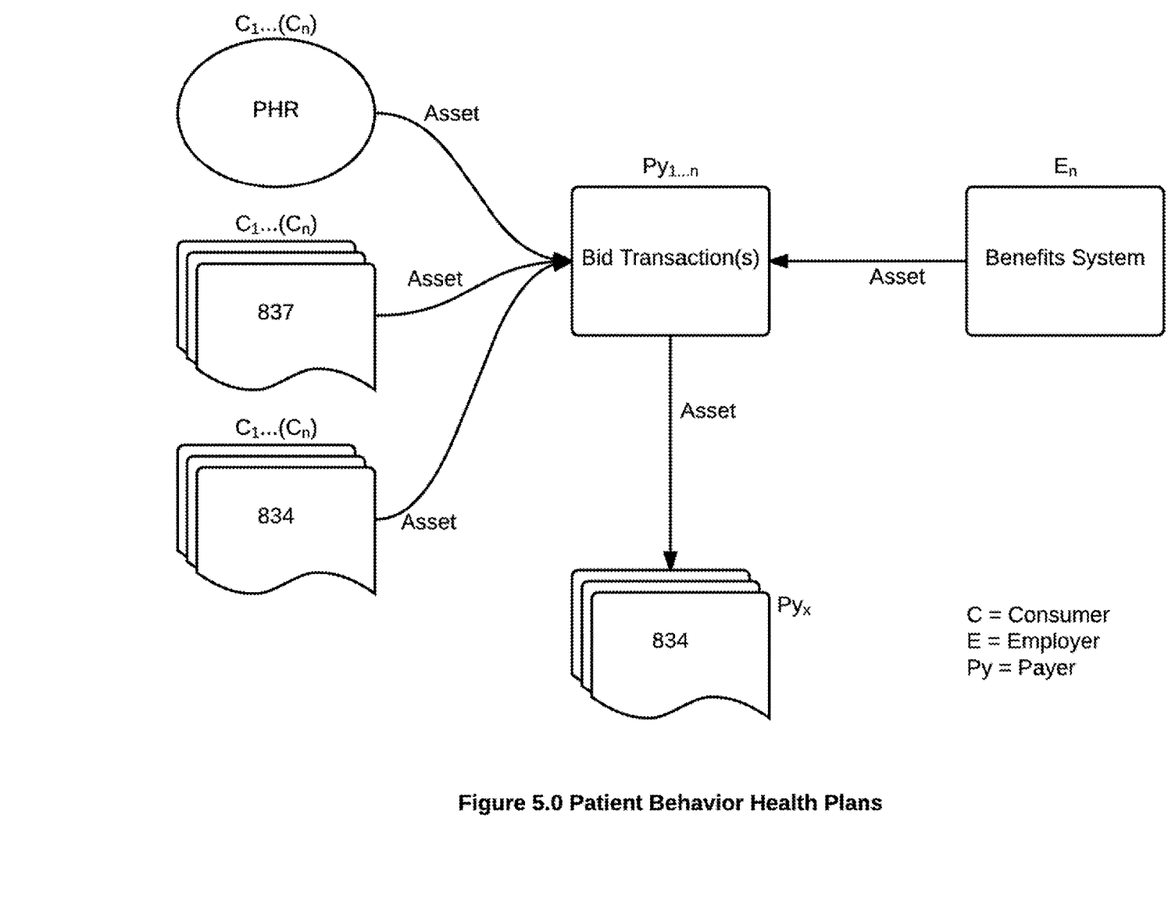

With the advent of personal health trackers, new health plans are rewarding consumers for taking an active part in their wellness. Similar to car insurance plans that offer discounts for installing a driving monitor, e.g. Progressive Snapshot® (https://www.progressive.com/auto/snapshot/), these plans are typically facilitated by the manufacturers of fitness tracking devices and partnerships have been formed, e.g. Fitbit Wellness Partners (http://www.fitbit.com/fitbit-wellness/partners.) The Health BlockChain network will facilitate a more open distribution of the consumers wellness data and protect it as PHR must be, and therefore prevent lock-in of consumers, providers and payers to a particular device technology or health plan. In particular, since PHR data is managed on the blockchain a consumer and/or company can grant access to a payer to this data such that the payer can perform group analysis of an individual or an entire company's employee base including individual wellness data and generate a risk score of the individual and/or organization. Having this information, payers can then bid on insurance plans tailored for the specific organization. Enrollment then, also being managed on the blockchain, can become a real-time arbitrage process as shown in FIG. 5.0 instead of the now typical yearly administrative overhead process.

The pseudo code for the smart contract to implement a patient behavior based health plan is as follows.

```
phr_info[ ] = transaction.data.phr_inputs
claim_info[ ] = transaction.data.claim_inputs
enrollment_info[ ] = transaction.data.enrollment_inputs
consumers = keys(phr_info, claim_info, enrollment_info)
for each consumer in consumers do
    risk_score += calculate_risk_for(consumer)
plan_detail = calculate_plan_for(risk_score)
return submit_transaction(consumers, plan_detail)
```

Patient and Provider Data Sharing

A patient's Health BlockChain wallet stores all assets, which in turn store reference ids to the actual data, whether clinical documents in HL7 or FHIR format, wellness metrics of activity and sleep patterns, or claims and enrollment information. These assets and control of grants of access to them is afforded to the patient alone. Given the open distribution of the Health BlockChain, any participating provider can be given full or partial access to the data instantaneously and automatically via enforceable restrictions on smart contracts.

In today's typical doctor visit scenario where a new patient arrives for the first time the attending physician has no prior history except for what is documented in the paperwork completed by the patient while waiting to be seen. This is time consuming and takes away from the purpose of the visit.

Utilizing the Health BlockChain the access to a patient's PHR can be granted as part of scheduling an appointment, during a referral transaction or upon arrival for the visit. And, access can just as easily be removed, all under control of the patient.

Figure 60:
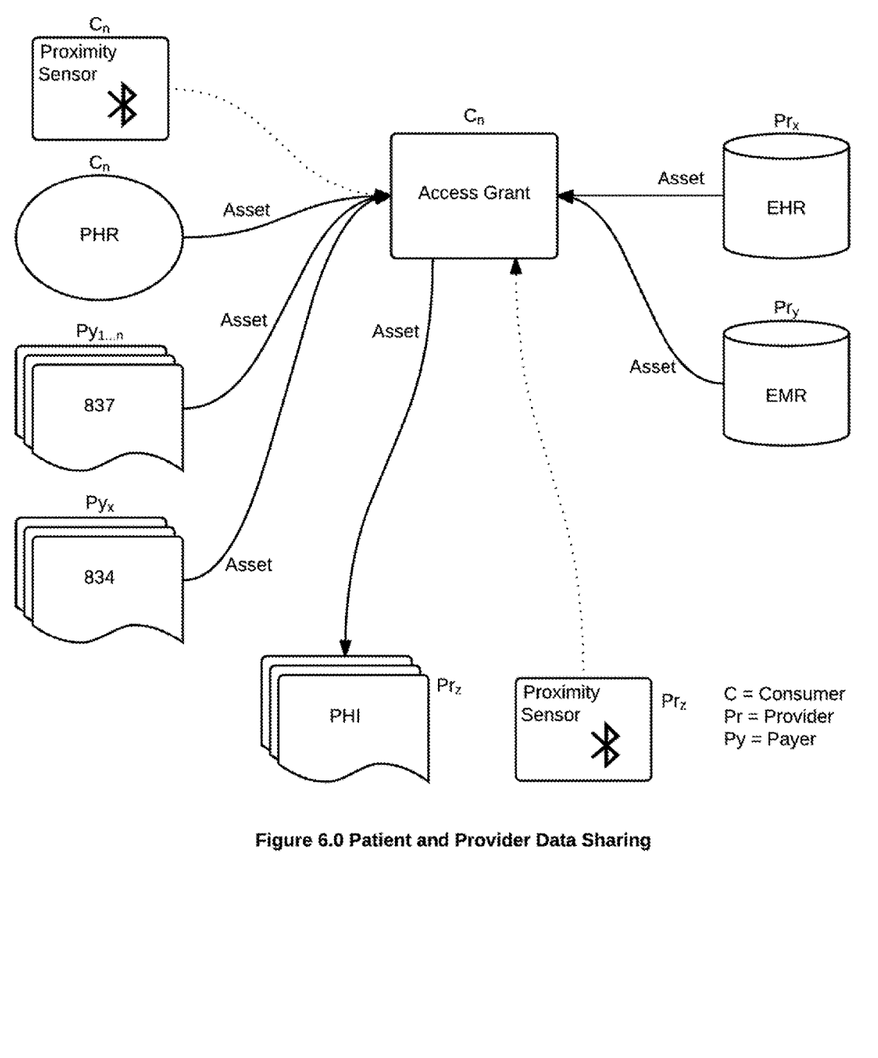

A scenario where upon arrival at the doctor's office a bluetooth proximity sensor can identify a patient running a mobile application on their personal bluetooth capable device which is a proxy for the patient's Health BlockChain wallet is shown in FIG. 6.0. This mobile wallet proxy can be configured to automatically notify the provider's office of arrival and grant access to the patient's PHR. At this point the attending physician will have access to the patient's entire health history.

The pseudo code for the smart contract to implement a patient and provider data sharing is as follows.

```
patient_sensor_state = transaction.data.patient_sensor_input
provider_sensor_state = transaction.data.provider_sensor_input
phr_data = transaction.data.phr_input
claim_data = transaction.data.claim_input
enrollment_data = transaction.data.enrollment_input
patient = transaction.data.patient_input
provider = transaction.data.provider_input
if patient_sensor_state is ON and provider_sensor_state is ON then
    if provider is in patient.trusted_provider_list( )
        patient.grant_access_to(provider)
        return phr_data, claim_data, enrollment_data
```

Patient Data Sharing

Patient's PHR data is valuable information for their personal health profile in order to provide Providers (Physicians) the necessary information for optimal health care delivery. In addition this clinical data is also valuable in an aggregate scenario of clinical studies where this information is analyzed for diagnosis, treatment and outcome. Currently this information is difficult to obtain due to the siloed storage of the information and the difficulty on obtaining patient permissions.

Figure 70:
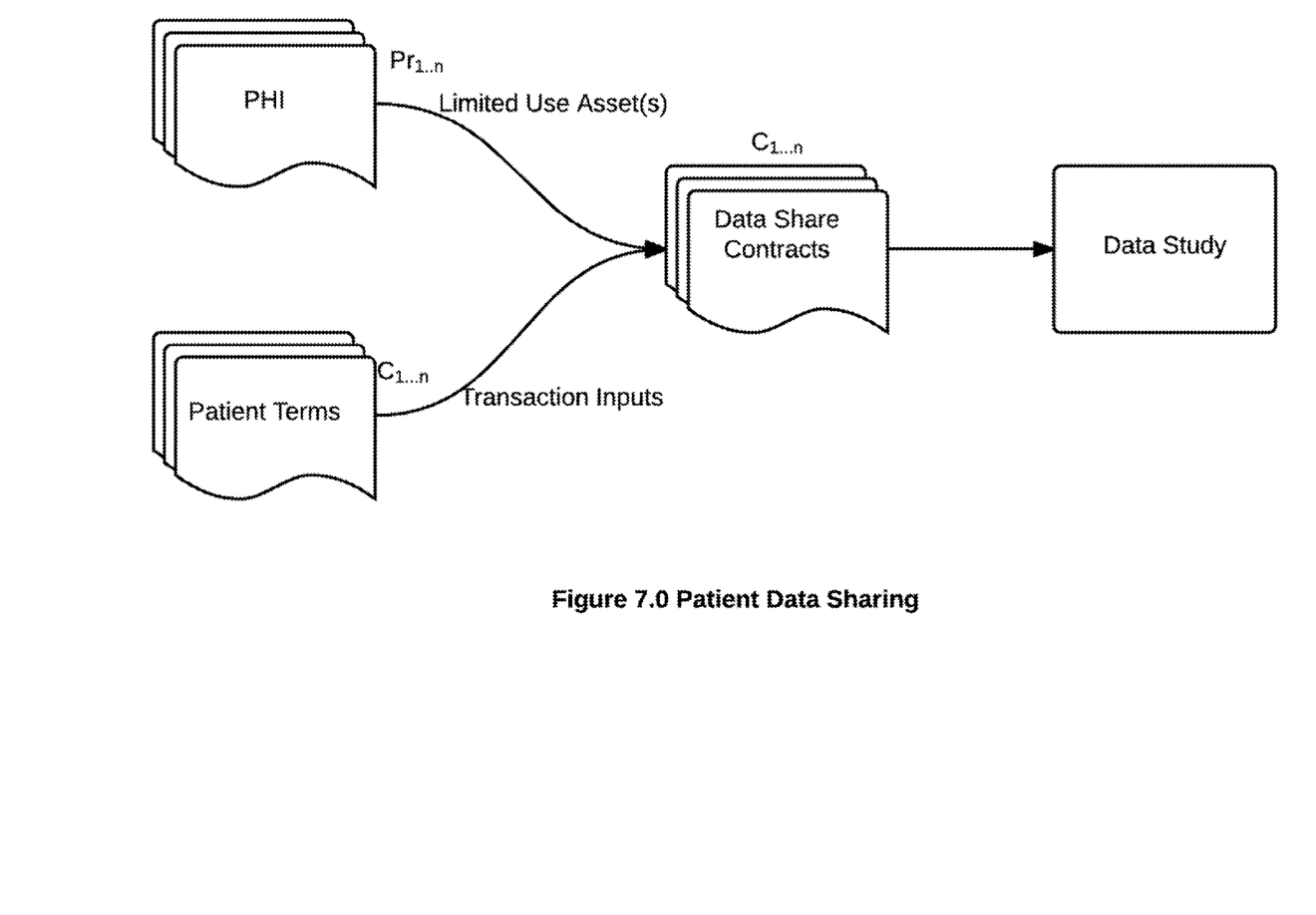

Given a patient Health BlockChain wallet that stores all assets as reference ids to the actual data. These assets can be included in an automated smart contract for clinical study participation or any other data sharing agreement allowed by the patient. The assets can be shared as an instance share by adding to the document a randomized identifier or nonce, similar to a one-time use watermark or serial number, a unique asset (derived from the original source) is then generated for a particular access request and included in a smart contract as an input for a particular request for the patient's health record information. A patient can specify their acceptable terms to the smart contract regarding payment for access to PHR, timeframes for acceptable access, type of PHR data to share, length of history willing to be shared, de-identification thresholds or preferences, specific attributes of the consumer of the data regarding trusted attributes such as reputation, affiliation, purpose, or any other constraints required by the patient. Attributes of the patient's data are also advertised and summarized as properties of the smart contract regarding the type of diagnosis and treatments available. Once the patient has advertised their willingness to share data under certain conditions specified by the smart contract it can automatically be satisfied by any consumer satisfying the terms of the patient and their relevance to the type of PHR needed resulting in a automated, efficient and distributed means for clinical studies to consume relevant PHR for analysis. This process shown in FIG. 7.0 turns a clinical study into an automated execution over the Health BlockChain for any desired time period that will terminate at an acceptable statistical outcome of the required attained significance level or financial limit.

The pseudo code for the smart contract to implement automated patient data sharing is as follows.

```
phi_data = transaction.data.phi_input
patient_data_sharing_terms = transaction.data.patient_data_sharing_terms_input
patient = transaction.data.patient_input
data_study = transaction.data.data_study_input
if data_study.requirments == patient_data_sharing_terms.allowances then
    patient.grant_access_to(data_study)
    return phi_data
```

Health BlockChain Data Elements

The actual data, assets, contracts, PII, etc. stored on the blockchain are actually resource identifiers which uniquely identify the data, location and access thereof as shown in FIG. 1.0. An application participating in the Health BlockChain that fully implements all of the features and stores and distributes actual data elements pointed to by the resource identifiers is shown in FIG. 2.0. This Health BlockChain application stack can also proxy through aggregation methods access to resource ids where data is stored in legacy PHR/PM/EMR/EHR and X12 EDI systems. An example of an implementation of the data structure for the block chain reduces to the following information:

Patients
Basic Demographics
First Name
Last Name
Middle Name
Prefix
Suffix
Gender
Birth Date
Address
Phone(s)
Email(s)
Insurance Information
Member ID
Group ID
Total deductible
Remaining deductible
Dependents
Health Records
Continuity of Care Document
Consultation Note
Discharge Summary
History and Physical Note
Operative Note
Procedure Note
Progress Note
Unstructured Documents
Claims History
Eligibility History
Marketplace Interactions
Specialties Searched
Conditions Searched
Purchases made
Log in frequency
Providers rated/reviewed
Self Reported Health Statistics Via Wearable APIs
BMI
Smoker status
Activity Level
Wellness program memberships
Financial Information FICO Credit Score
Credit reports
Assets/Debts
Lending data from Lending Club
Social Network Interaction Data
twitter, facebook, linked
Wearable API Data
Measured activity level
Sleep cycles
Providers
Provider Demographics
First Name
Last Name
Middle Name
Prefix
Suffix
Gender
Birth Date
Address
Phone(s)
Email(s)
Licensing
Medical Education
Where and when they went to medical school
Graduation date
Where and when they did their residencies/fellowships
Specialties
Credentials
Certifications
Hospital affiliations
Pricing
Submitted and paid prices from medicare
Cash prices
Services listed on the marketplace
Responses to requests for quote
Ratings, Reviews, Recognitions
Reviews and ratings from marketplace
Malpractice Sanctions from state licensure bodies we receive from the American Medical Association
Ratings and Reviews
Claims Statistics
Number of claims submitted, submitted price, reimbursed price per procedure
Number of rejected claims per procedure
Payers (Aka Insurance Carriers, Trading Partners)

With the processing of X12 health transactions, the system can easily obtain the following information:

Payment Statistics: How much does payer X pay on average for procedure Y.

Statistics about time taken to process claims (i.e. average processing time, average time per procedure, etc.)

Statistics about rejected claims. Analysis of claims in general and claims segmented by payer will probably allow us to build predictive models for determining the probability that a claim will be rejected.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media.

Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

The invention claimed is:

1. A system for a decentralized autonomous healthcare, comprising:
   a computer system having a plurality of off-chain health data sources some of which contain personal health data whose access is controlled by a patient, the personal health data including consultation data, medical history data, medical procedure data, claims data and eligibility data;
   a plurality of health blockchain network components implemented on a computer system that interface with the plurality of off-chain health data sources, each health blockchain network component comprising a plurality of blocks forming a linked list with each block having a header with a cryptographic hash of a prior block in the plurality of blocks and a healthcare transaction coupled to the header and each health blockchain network component maintains cryptographic proof of a valid healthcare transaction;
   wherein one of the plurality of health blockchain network components performs a healthcare transaction using a healthcare transaction protocol using the personal health data in the off-chain health data sources when authorization is granted to the personal health data and the one healthcare blockchain network component executes an automated patient data sharing smart contract that grants access to an authorized user to the personal health data stored in the off-chain health data sources if the authorized user satisfies a set of terms contained in the smart contract; and wherein the plurality of health blockchain network components perform side chaining in which a first health blockchain network component validates the data from a second health blockchain network component during the healthcare transaction.

2. The system of claim 1 further comprising a plurality of computer system that form a peer to peer network.

3. The system of claim 1 further comprising an application, remote from each health blockchain network component that request a performance of the healthcare transaction using the healthcare transaction protocol.

4. The system of claim 1, wherein the healthcare transaction is an X12 health transaction.

5. The system of claim 1 further comprising a smart contract executing at one of the plurality of health blockchain network components that grants access to the personal health data.

6. The system of claim 1, wherein the plurality of health blockchain network components store one or more of a resource identifier for a resource stored in the off-chain health data sources, an asset signature and an authorization grant for access to the personal health data.

7. The system of claim 1, wherein the automated patient data sharing smart contract further comprises a clinical study participation smart contract.

8. A method for providing a decentralized autonomous healthcare system, the method comprising:

providing a computer system having a plurality of off-chain health data sources some of which contain personal health data whose access is controlled by a patient wherein the personal health data including consultation data, medical history data, medical procedure data, claims data and eligibility data and a plurality of health blockchain network components implemented on the computer system that interface with the plurality of off-chain health data sources, each health blockchain network component comprising a plurality of blocks forming a linked list with each block having a header with a cryptographic hash of a prior block in the plurality of blocks and a healthcare transaction coupled to the header and each health blockchain network component maintains cryptographic proof of a valid healthcare transaction;

performing, using one of the plurality of health blockchain network components, a healthcare transaction using a healthcare transaction protocol using the personal health data in the off-chain health data sources when authorization is granted to the personal health data;

executing, by one of the plurality of health blockchain network components, an automated patient data sharing a smart contract that grants access to an authorized user to the personal health data stored in the off-chain health data sources if the authorized user satisfies a set of terms contained in the smart contract; and performing, by the plurality of health blockchain network components, side chaining in which a first health blockchain network component validates the data from a second health blockchain network component during the healthcare transaction.

9. The method of claim 8 further comprising providing a plurality of computer system that form a peer to peer network.

10. The method of claim 8 further comprising requesting, using an application remote from each health blockchain network component, a performance of the healthcare transaction using the healthcare transaction protocol.

11. The method of claim 8, wherein the healthcare transaction is an X12 health transaction.

12. The method of claim 8 further comprising executing a smart contract at one of the plurality of health blockchain network components that grants access to the personal health data.

13. The method of claim 8, wherein the plurality of health blockchain network components store one or more of a resource identifier for a resource stored in the off-chain health data sources, an asset signature and an authorization grant for access to the personal health data.

14. The method of claim 8, wherein the automated patient data sharing smart contract further comprises a clinical study participation smart contract.

* * * * *